(12) United States Patent
Mulone

(10) Patent No.: US 8,287,573 B2
(45) Date of Patent: Oct. 16, 2012

(54) SYSTEM AND METHOD FOR MANDIBULAR BONE TRANSPORT RECONSTRUCTION

(75) Inventor: Timothy D. Mulone, Dallas, TX (US)

(73) Assignee: Craniotech ACR Devices, LLC, Dallas, TX (US)

( * ) Notice: Subject to any disclaimer, the term of this patent is extended or adjusted under 35 U.S.C. 154(b) by 928 days.

(21) Appl. No.: 12/336,056

(22) Filed: Dec. 16, 2008

(65) Prior Publication Data

US 2010/0152734 A1   Jun. 17, 2010

(51) Int. Cl.
*A61B 17/66* (2006.01)
(52) U.S. Cl. .................................. 606/282; 606/105
(58) Field of Classification Search .............. 606/282, 606/105; 600/237–238; 254/85, 260
See application file for complete search history.

(56) References Cited

U.S. PATENT DOCUMENTS

| | | | |
|---|---|---|---|
| 5,364,396 A | 11/1994 | Robinson et al. | 606/53 |
| 6,053,919 A | 4/2000 | Talos et al. | 606/71 |
| 6,277,124 B1 | 8/2001 | Haag | 606/105 |
| 6,355,036 B1 | 3/2002 | Nakajima | 606/57 |
| 6,918,910 B2 | 7/2005 | Smith et al. | 606/60 |
| 7,182,785 B2 | 2/2007 | Elsalanty et al. | 623/17.17 |
| 2005/0203628 A1 | 9/2005 | Elsalanty et al. | 623/17.17 |
| 2006/0282073 A1* | 12/2006 | Simanovsky | 606/61 |
| 2007/0043370 A1 | 2/2007 | Ueda et al. | 606/71 |

FOREIGN PATENT DOCUMENTS

| | | |
|---|---|---|
| WO | WO 97/27811 | 8/1997 |
| WO | WO 01/21082 A1 | 3/2001 |
| WO | WO 01/30249 | 5/2001 |

OTHER PUBLICATIONS

Notification of Transmittal of the International Search Report and the Written Opinion of the International Searching Authority or the Declaration; PCT/US2009/068043; 15 pages, May 3, 2010.
Brochure, "The Thread-Lock™ Transport Distractor," KLS Martin L.P., manufactured by Medical Modeling LLC, 4 pages.
Genecov, David, et al., Distraction Osteogenesis; The Clinical Experience at the International Craniofacial Institute—Dallas, Texas, Distraction Osteogenesis Interactive Course on CD ROM, GlobalMed Net 1:236-254 (1999) available at http://www.globalmednet.com/do-cdrom/Clinical/MandLeng/Genecov/gen001.htm, 1999.
Hidding, J., et al., "Intraoral Vertical Bone Distraction of the Alveolar Ridge", Distraction Osteogenesis Interactive Course on CD ROM, GlobalMed Net 1999, available at http://www.globalmednet.com/docdrom/Clinical/Alveolar/Hidding/hd0001.htm, 1999.

(Continued)

*Primary Examiner* — Andrew Yang
(74) *Attorney, Agent, or Firm* — Baker Botts L.L.P.

(57) ABSTRACT

A mandibular bone transport device includes a carriage block and a set of flanges operable to couple to a transport bone plate. The device also includes a flexible connector configured to flexibly couple the set of flanges to the carriage block such that the flanges can be displaced relative to the carriage block when a force is applied. Further, the device includes a screw housed within the carriage block which is operable to engage a track and operable to advance the carriage block along the track. The device also includes a coupling configured to engage the screw and operable to rotate the screw when rotational force is applied to the coupling.

21 Claims, 6 Drawing Sheets

OTHER PUBLICATIONS

Guerrero and Bell, Intraoral Mandibular Bone Transport Using the DynaForm™ Distraction Device: A Case Report, Distraction Osteogenesis Interactive Course on CD ROM, GlobalMed Net (1999) available at http://www.globalmednet.com/do-cdrom/Clinical/Transp/guerrero/gr001.htm, 1999.

Klein, C., et al., "Initial experiences using a new implant based distraction system for alveolar ridge augmentation", Int J Oral Maxillofac Surg 30(2): 167-9 (2001).

Ayoub, A.F., et al., "Segmental mandibular reconstruction by microincremental automatic distraction osteogenesis: an animal study," British Journal of Oral and Maxillofacial Surgery (2001) 39, 356-364, Accepted Apr. 19, 2001 Published online Jul. 5, 2001.

Rubio-Bueno, P., et al., "Scientific Foundations, Experimental Mandibular Regeneration by Distraction Osteogenesis with Submerged Devices: Preliminary Results of a Canine Model," The Journal of Craniofacial Surgery, vol. 13, No. 2, 7 pages, Mar. 2002.

Müller, M.-C., et al., "A comparison of two types of free bone grafts as transport discs in segmental distraction for reconstruction of calvarial bone defects: an experimental study," Arch Orthop Trauma Surg (2004) 124, DOI 10.1007/s00402-004-0749-3, 665-674, Published online Oct. 28, 2004.

Kuriakose, M.A., et al., "Reconstruction of Segmental Mandibular Defects by Distraction Osteogenesis for Mandibular Reconstruction," Head & Neck, 9 pages, Oct. 2003.

Herford, Alan S., "Use of a Plate-Guided Distraction Device for Transport Distraction Osteogenesis of the Mandible", J Oral Maxillofac Surg 62(4):412-20 (Apr. 2004).

Li, J., et al., "Reconstruction of mandibular symphyseal defects by trifocal distraction osteogenesis: an experimental study in Rhesus," International Journal of Oral & Maxillofacial Surgery, 0901-5027/020159 + 06, 6 pages, 2006 © 2005.

* cited by examiner

SYSTEM AND METHOD FOR MANDIBULAR BONE TRANSPORT RECONSTRUCTION

TECHNICAL FIELD

This invention relates generally to bone reconstruction and more particularly to a system and method for mandibular bone transport reconstruction.

BACKGROUND

Distraction osteogenesis is a process of new bone formation between two bone segments, when they are gradually separated by incremental traction. This pattern of bone elongation allows the surrounding soft tissues to adjust to the new skeletal dimensions through the series of adaptive changes called distraction histiogenesis. Active histiogenesis has been shown to occur in various soft tissues including skeletal muscles, nerves, blood vessels, periodontal ligament, and gingiva. The result will be the synthesis of new bone with a cover of periostium and soft tissues (mucosa, muscles, etc.) as well as new vascular and nerve supply. Distraction osteogenesis has been performed for various portions of the skeletal system. For example, distraction osteogenesis has been used in mandibular applications when portions of a mandible have been excised.

Overview

A mandibular bone transport device includes a carriage block and a set of flanges operable to couple to a transport bone plate. The device also includes a flexible connector configured to flexibly couple the set of flanges to the carriage block such that the flanges can be displaced relative to the carriage block when a force is applied. Further, the device includes a screw housed within the carriage block which is operable to engage a track and operable to advance the carriage block along the track. The device also includes a coupling configured to engage the screw and operable to rotate the screw when rotational force is applied to the coupling.

A method for mandibular distraction osteogenesis includes securing flanges to a portion of a mandible. It also includes securing a first end of a curved bone reconstruction plate to a first mandibular bone segment. The curved bone reconstruction plate includes a threaded track. Further, it includes securing a second end of the curved bone reconstruction plate to a second mandibular bone segment. In addition, it includes flexibly coupling the flanges to a carriage block using a flexible connector. The carriage block houses a screw operable to engage the threaded track and advance the carriage block along the threaded track. Also, the method includes rotating the screw to advance the carriage block along a curved region of the track such that the carriage block is displaced relative to the flanges as the carriage block advances along the curved region of the track.

Depending on the specific features implemented, certain embodiments may exhibit some, none, or all of the following technical advantages. For example, certain embodiments may allow a bone transport device to advance along curved tracks in addition to or as an alternative to straight tracks. In certain embodiments, a flexible coupling also provides the ability to advance the bone transport device while it is negotiating a curved portion of the track. Other technical advantages will be readily apparent to one skilled in the art from the following figures, description, and claims.

BRIEF DESCRIPTION OF THE DRAWINGS

Reference is now made to the following description taken in conjunction with the accompanying drawings, wherein like reference numbers represent like parts and in which.

DETAILED DESCRIPTION

Figure 1:
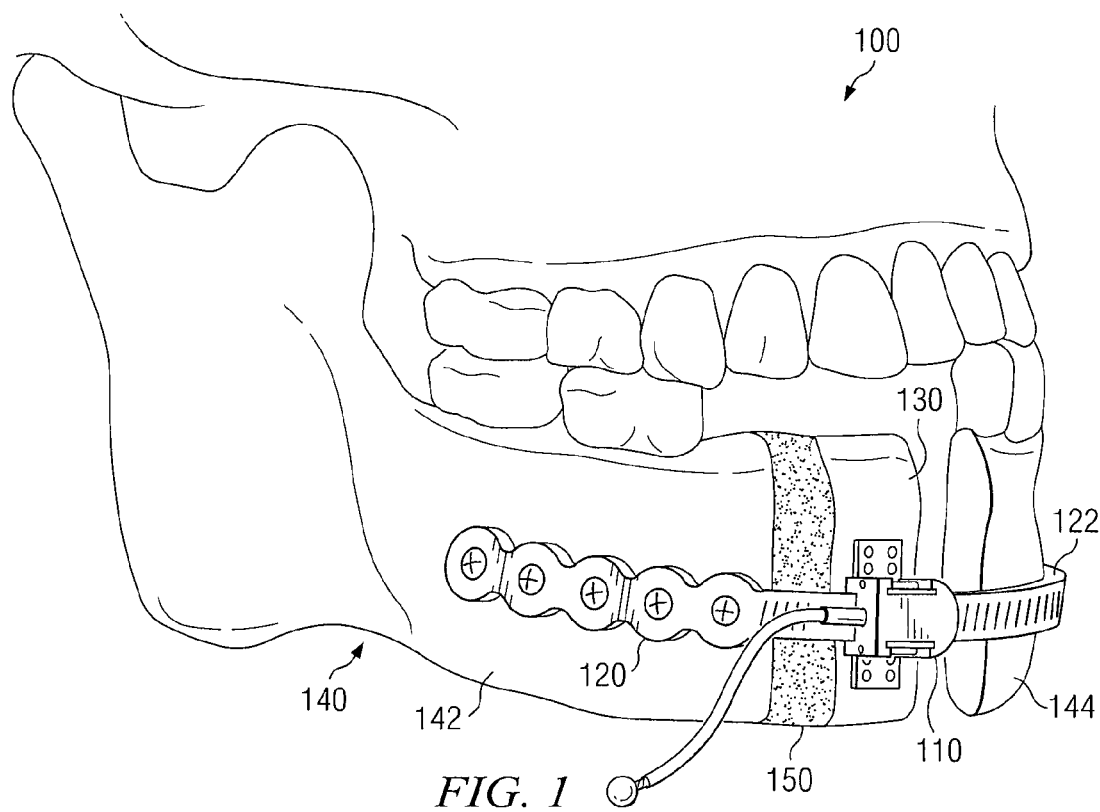
FIG. 1 illustrates an example system for mandibular bone reconstruction.

FIG. 1 illustrates an example system 100 for mandibular bone reconstruction. System 100 includes mandibular bone transport device 110 and bone reconstruction plate 120. Example bone reconstruction plate 120 includes track 122. In some embodiments, bone reconstruction plate 120 may be secured to mandible 140. In certain embodiments, mandible 140 includes first mandibular bone segment 142 and second mandibular bone segment 144.

In operation, transport device 110 is secured to track 122 and transport bone plate 130 is coupled to transport device 110. As transport device 110 advances along track 122, in certain embodiments, growth 150 may form in the space between transport bone plate 130 and mandible 140. In certain embodiments, lubricants such as titanium nitride may be used to facilitate the advancement of transport device 110 along track 122.

Transport bone plate 130, in particular embodiments, may be a bone plate severed from mandible 140. In some embodiments, growth 150 is new bone which forms in the gap between plate 130 and mandible 140 as a result of the distraction osteogenesis process. Thus, in various embodiments, a gap in mandible 140 may be reconstructed by advancing transport bone plate 130 along a path between two bone segments defined by track 122.

Figure 2:
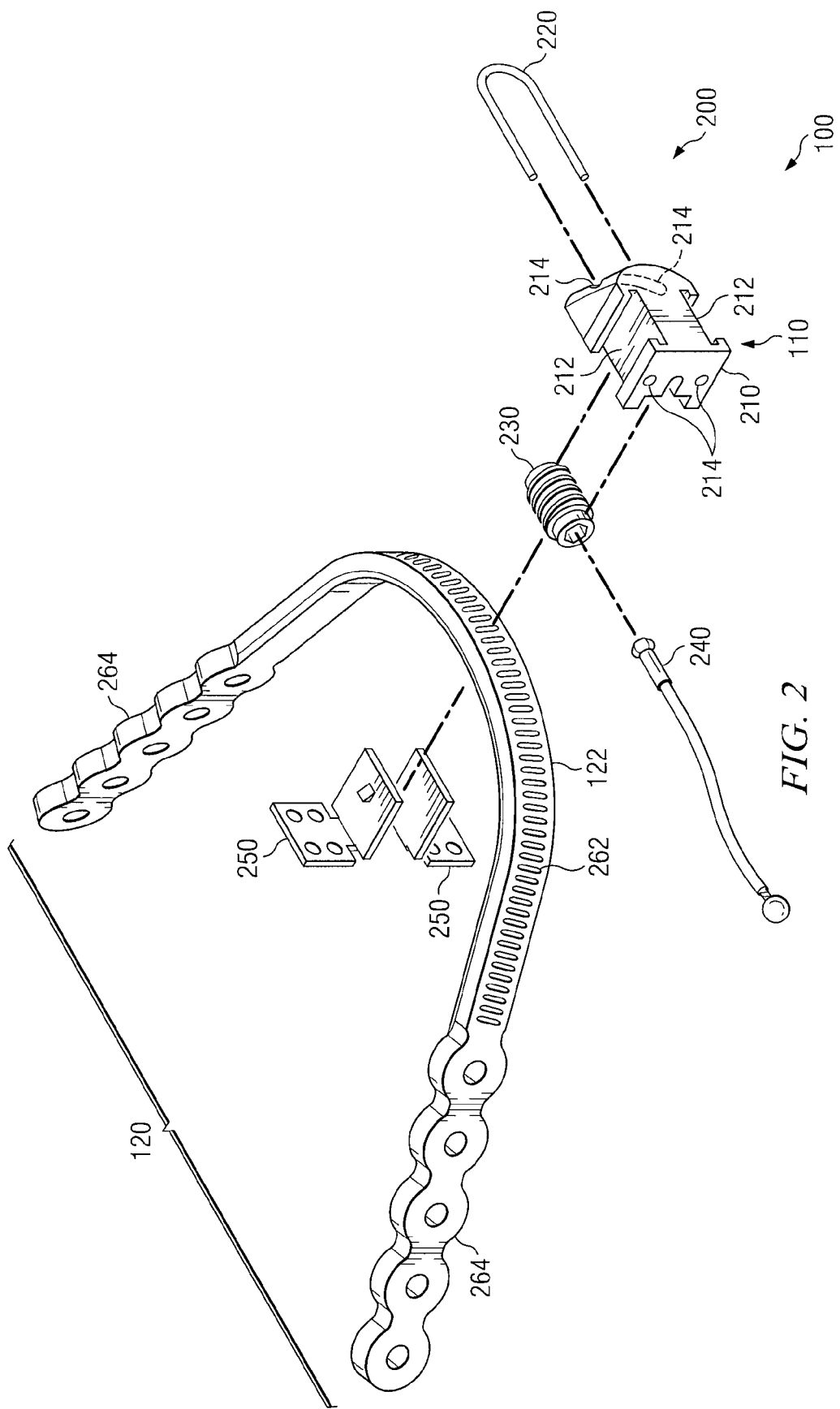
FIG. 2 illustrates an exploded view of an example system for mandibular bone reconstruction.

FIG. 2 illustrates an exploded view of example system 100 for mandibular bone reconstruction. Transport device 110, in various embodiments, may include carriage block 210, flexible connector 220, screw 230, and coupling 240. In certain embodiments, transport device 110 is coupled to flanges 250.

Although any appropriate biocompatible material may be used, carriage block 210, in some embodiments, may be composed of Grade 304 stainless steel. In some embodiments, carriage block 210 is formed with a sloped frontal portion which may facilitate its advancement through soft tissue during reconstruction by presenting an acute leading edge.

Flexible connector 220 is, in some embodiments, a spring operable to bend in a manner that allows carriage block 210 to travel around curved portions of track 122, as described further below. In certain embodiments, flexible connector 220 may also serve to couple flanges 250 and carriage block 210. Although any appropriate biocompatible material may be used, in some embodiments, flexible connector 220 may be formed of 032 gauge stainless steel wire. Flexible connector 220, though, may also be formed from different gauges of stainless steel wire or other suitable materials, such as composites. In certain embodiments, flexible connector 220 may be formed in different shapes. In certain embodiments, flexible connector 220 may include multiple parts, not just one continuous part as depicted; this may provide an advantage in that the different parts of flexible connector 220 may each have a different modulus of elasticity. Flexible connector 220, in particular embodiments, may be inserted into holes 214. In some embodiments, holes 214 are formed on carriage block 210 using a punch. In some embodiments, flexible connector 220 may be an elastic band.

Bone reconstruction plate 120, in certain embodiments, includes track 122. In certain embodiments, track 122 includes threaded portion 262. In some embodiments, track 122 is coupled to mandible 140 via openings in securing portions 264 by utilizing 2.3-2.7 titanium screws. In other embodiments, securing portions 264 may be coupled to the jaw bone using differently-dimensioned titanium screws or other suitable attaching devices. A 5.5° to 10.5° square thread, in certain embodiments, may be included in threaded portion 262. In certain embodiments, threaded portion 262 includes a 7.5° square thread. In certain embodiments, a square thread may allow for the reduction of forces applied to the track perpendicular to the advancement of screw 230. Alternatively, a 60° thread, in various embodiments, may be included in threaded portion 262. In other embodiments, threaded portion 262 may include other configurations suitable for advancing carriage block 210. In some embodiments, track 260 may be formed by CNC milling a titanium alloy to form securing portions 264 and then bending the titanium; afterwards, threaded portion 262 may be formed using Electrical Discharge Machining. The titanium alloy, in various embodiments, may be medical grade titanium alloy 6ALV4.

In some embodiments, carriage block 210 may house screw 230 while screw 230 engages track 122. Further, coupling 240 may engage screw 230 and may be used to advance screw 230 along track 122 by applying rotational force to screw 230. Flanges 250, in certain embodiments, may engage carriage block 210 through guideways 212 and flexible connector 220. Carriage block 210 may also be configured to receive flexible connector 220 through holes 214.

Figure 3:
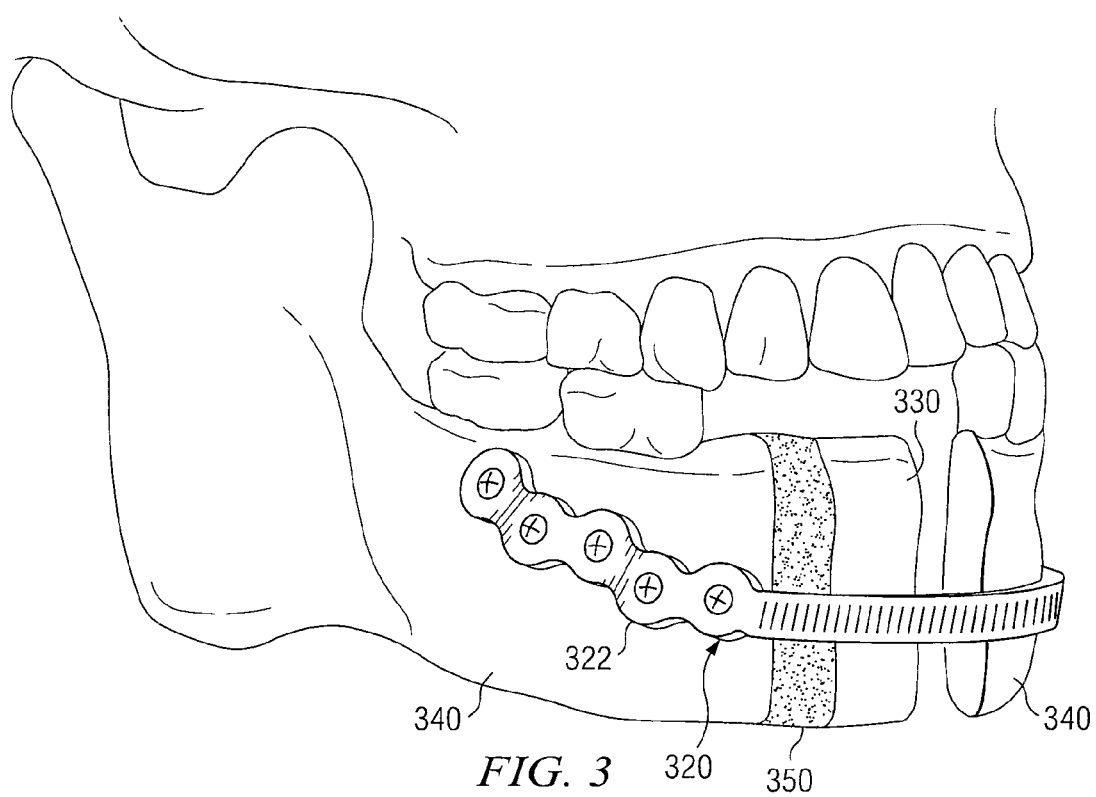
FIG. 3 illustrates an example bone reconstruction plate for use with an example system for mandibular bone reconstruction.

FIG. 3 illustrates an example bone reconstruction plate 320 for use with an example system for mandibular bone reconstruction. As shown in FIG. 3, in certain embodiments, the openings in securing portions 322 may be staggered. In other embodiments, securing portions 322 may be curved such that the openings in securing portions 322 are not aligned. In some embodiments, having the openings in securing portions 322 not aligned may increase stability.

Figure 4:
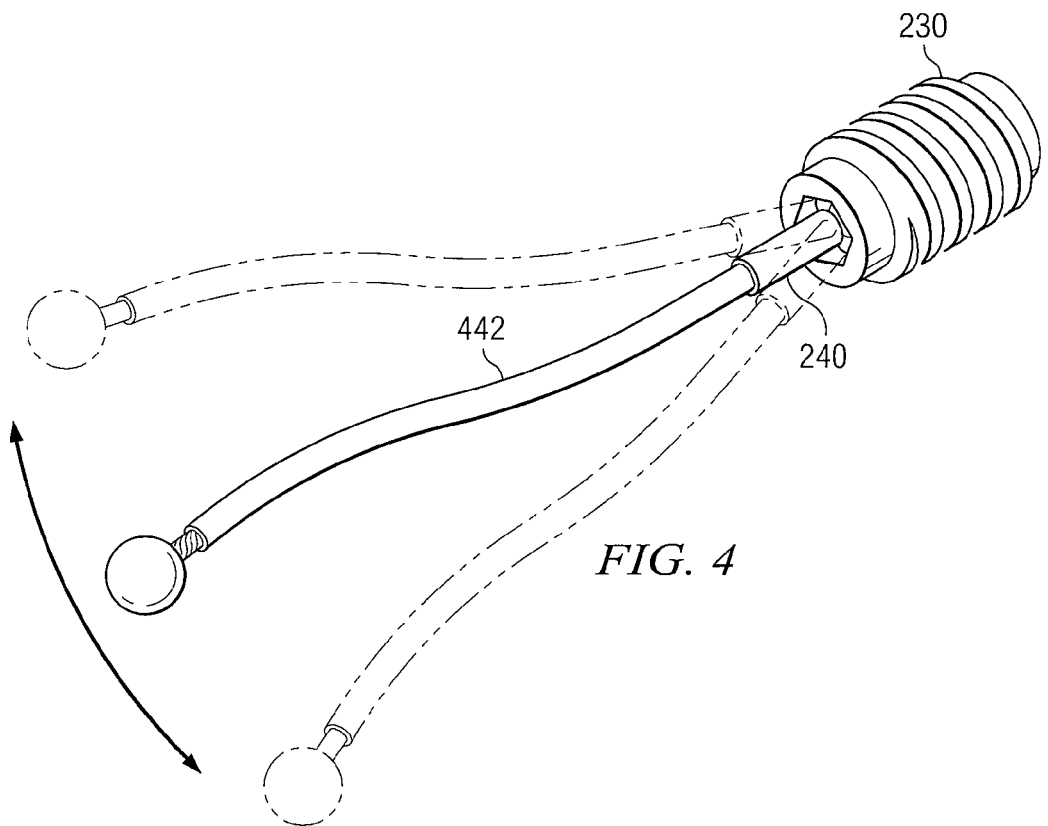
FIG. 4 illustrates an example screw engaged by an example coupling.
Figure 5A:
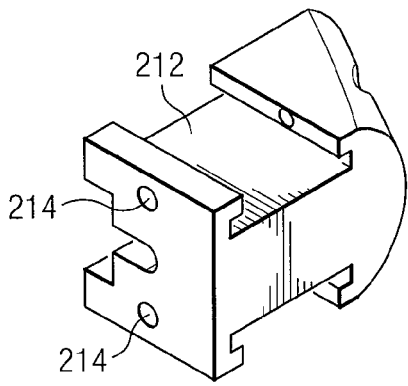
FIGS. 5A-5D illustrate alternative views of an example carriage block.
Figure 5B:
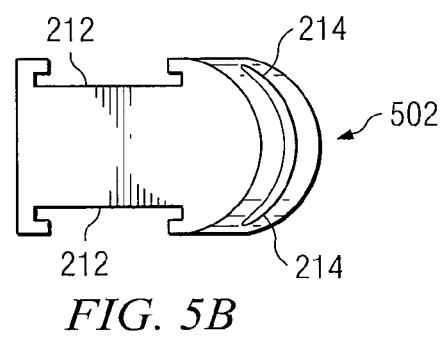
Figure 5C:
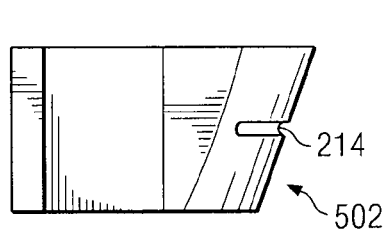
Figure 5D:
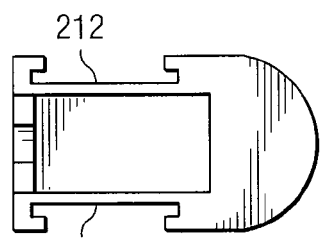

FIG. 4 illustrates example screw 230 engaged by example coupling 240. In various embodiments, as depicted, screw 230 receives the head of coupling 240. Driving portion 442 may be coupled to the head of coupling 240 by, for example, crimping. Coupling 240, in some embodiments, is configured to be flexible such that driving portion 442 may move while coupling 240 remains coupled to screw 230. In certain embodiments, the connection between screw 230 and coupling 240 is flexible, as shown in FIG. 4. In various embodiments, driving portion 442 may be an activation cable which, when operated by utilizing a knob, may allow for the transport device to be activated. In some embodiments, the activation cable may be covered with a teflon sheath. In certain embodiments, the activation cable may be accessible from outside of the mouth. A flexible coupling may be advantageous in that it may be accessed even as the transport device moves along a curved portion of the track. In various embodiments, coupling 240 has a hexagonal head. In certain embodiments, screw 230 and/or coupling 240 may be formed of Grade 304 stainless steel. In certain embodiments, however, the type of head of coupling 240 and the materials used in screw 230 and coupling 240 may be different.

FIGS. 5A-5D illustrate alternative views of example carriage block 210.

Figure 6:
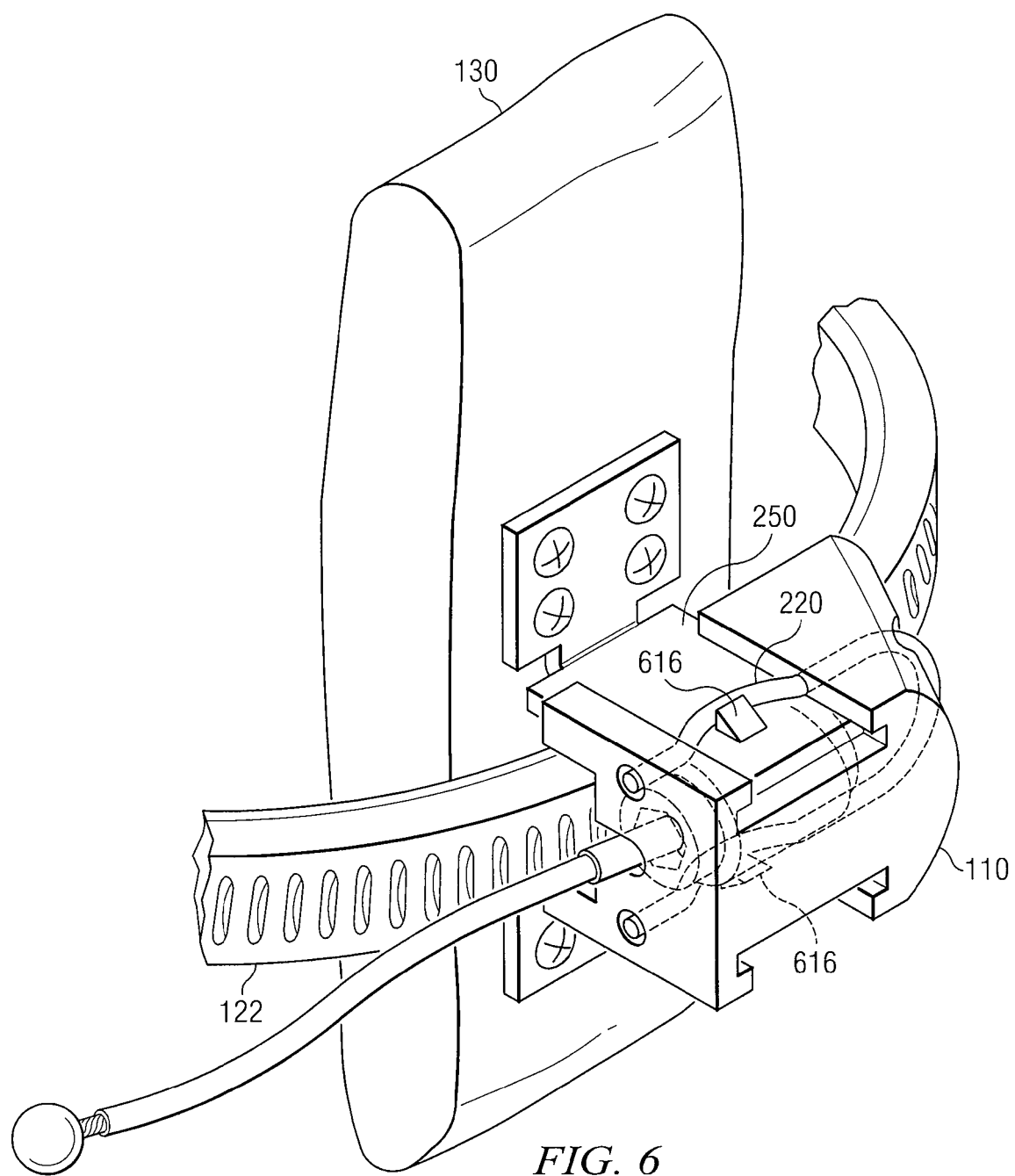
FIG. 6 illustrates an example transport device advancing along a curved portion of a track.

FIG. 6 illustrates one embodiment of transport device 110 advancing along a curved portion of track 122 with transport bone plate 130 secured to transport device 110. In certain embodiments, transport device 110 includes flexible connector 220 which may serve to couple flanges 250 to transport device 110; flexible connector 220 contacts flanges 250 through tabs 616. Transport bone plate 130 may be secured to flanges 150. In certain embodiments, the translational force causing transport device 110 to advance along the curved portion of track 122 may induce a tangential force upon flanges 250 and transport bone segment 130 because of contact between transport bone segment 130 or flanges 250 and the curved portion of track 122. In certain embodiments, a component force of the tangential force applied to flanges 250 is exerted perpendicular to the translational force advancing transport device 110 along track 122. This component force will cause flexible connector 220 to bend. In certain embodiments, flanges 250 and transport bone plate 130 are displaced with respect to transport device 110 due to the bending of flexible connector 220. This displacement reduces allows transport device 110 to continue to move along the curved portion of track 122.

Figure 7:
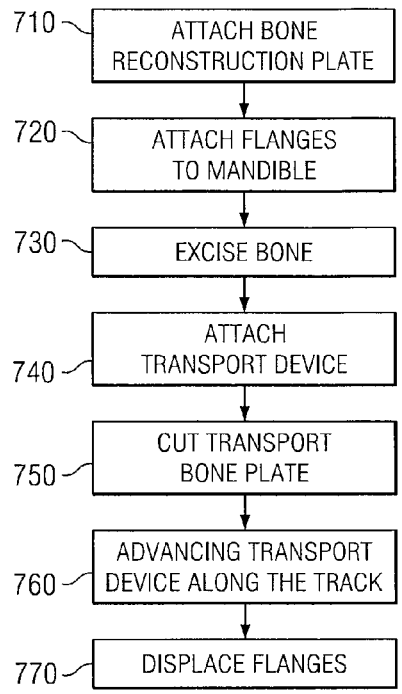
FIG. 7 is an example method for distraction osteogenesis.

FIG. 7 is an example method for distraction osteogenesis. In general, the steps illustrated in FIG. 7 may be combined, modified, or deleted where appropriate, and additional steps may also be added to the example operation. Furthermore, the described steps may be performed in any suitable order. At step 710, a bone reconstruction plate is attached to the mandible. In certain embodiments, the bone reconstruction plate may be attached to two mandibular bone segments. In certain embodiments, the bone reconstruction plate may be attached using screws, such as mini-screws. However, the bone reconstruction plate may be attached using other forms of attachment, such as adhesives. In certain embodiments, step 710 may be performed after a segment of bone is excised (as in step 730) or after the flanges are attached to the mandible (as in step 720).

At step 720, flanges are attached to the mandible. The flanges may be attached to the portion of the mandible which will be used as the transport bone plate. In certain embodiments, this step may be performed before the bone reconstruction plate is secured to the mandible (as in step 710) or after the transport device is attached to the bone reconstruction plate (as in step 740). In certain embodiments, the flanges may be attached using screws, such as mini-screws. However, flanges may be attached using other forms of attachment, such as adhesives.

At step 730, a segment of bone is excised from the mandible. In certain embodiments, this may occur before the bone reconstruction plate is attached (as in step 710). At step 740, the transport device is attached to the track of the bone reconstruction plate and coupled to the flanges. In certain embodiments, the transport device is flexibly coupled to the flanges using a spring. In certain embodiments, the transport device includes a screw which engages the track of the bone reconstruction plate. In certain embodiments, the transport device includes pawls which engage the track of the bone reconstruction plate, as described further below.

At step 750, the transport bone plate is cut. In certain embodiments, this may occur before the flanges are attached to the mandible (as in step 720) or before the bone reconstruction plate is attached to the mandible (as in step 710).

At step 760, the transport device and flanges are advanced along the track. Prior to this, the flanges have been secured to the transport bone plate using a flexible connector such that the transport bone plate advances along with the transport device and flanges. In certain embodiments, the transport device includes a coupling coupled to the screw which is rotated and causes the transport device to advance along the track. In certain embodiments, the transport device includes a cam head which is coupled to pawls which advance the transport device in a ratchet-like manner, as described further below. In certain embodiments, as the transport device advances along the track, new bone growth forms in the gap created due to the advancement of the transport bone plate.

In certain embodiments, the transport device may advance along a curved portion of the track. At step 770, the flanges are displaced relative to the carriage block of the transport device as the transport device advances along a curved portion of the track. In certain embodiments, the translational force causing the transport device to advance along the curved portion of the track may induce a tangential force upon the flanges and transport bone segment because of contact between the transport bone segment or the flanges and the curved portion of the track. In certain embodiments, a component force of the tangential force applied to the flanges is exerted perpendicular to the translational force advancing the transport device along the track. This component force may cause the flexible connector to bend, which may allow for the flanges to be displaced away from the transport device.

Figure 8:
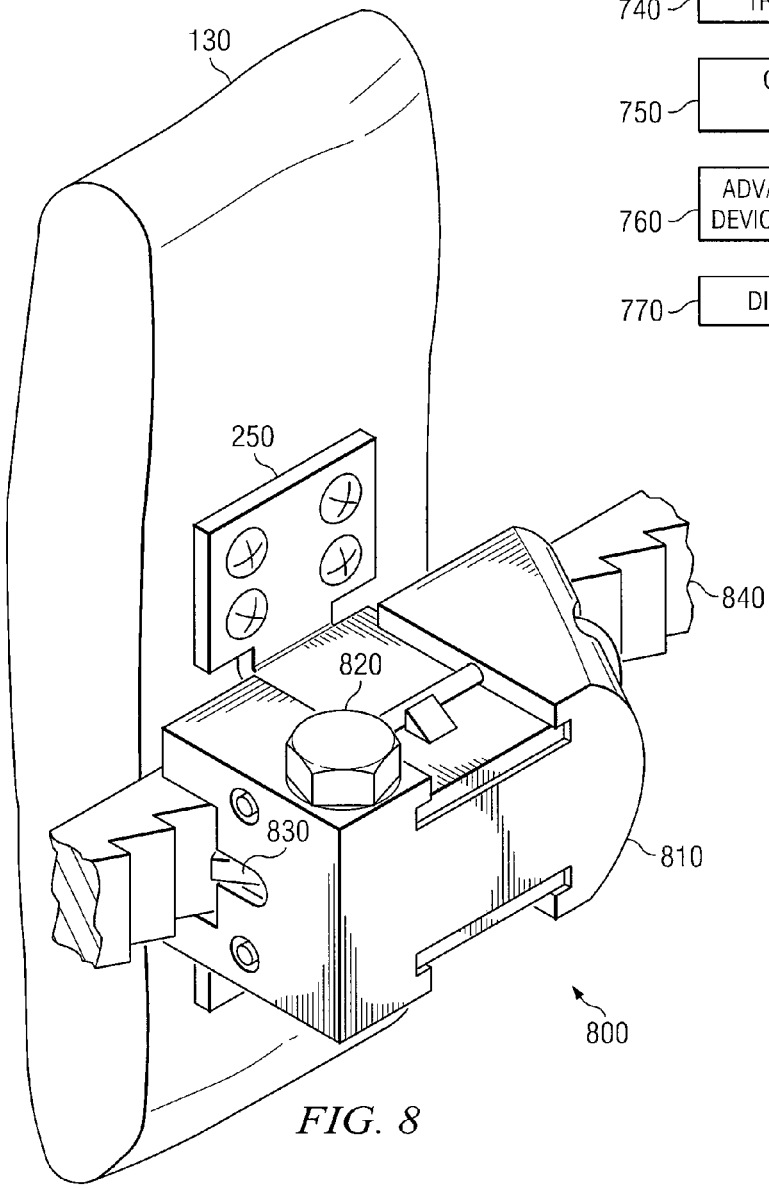
FIG. 8 illustrates another example system for mandibular bone reconstruction.

FIG. 8 illustrates another example system 800 for mandibular bone reconstruction. In the example shown, system 800 includes transport device 810, track 840, flanges 250, cam head 820, actuating pawls 830, and transport bone plate 130. In various embodiments, transport bone plate 130 is advanced along track 840 by transport device 810. In certain embodiments, transport device 810 includes cam head 820 and actuating pawls 830. Cam head 820 is operated in a ratchet-like manner to advance transport device along track 840 by manipulating actuating pawls 830. In particular embodiments, utilizing the depicted ratcheting mechanism to advance transport device 810 along track 840 may provide an advantage in that the ratcheting mechanism may be easily accessible by the operator as a result of the placement of cam head 820. Further, in certain embodiments, the use of the depicted ratcheting mechanism may only allow transport device 810 to move forward along track 840.

Figure 9:
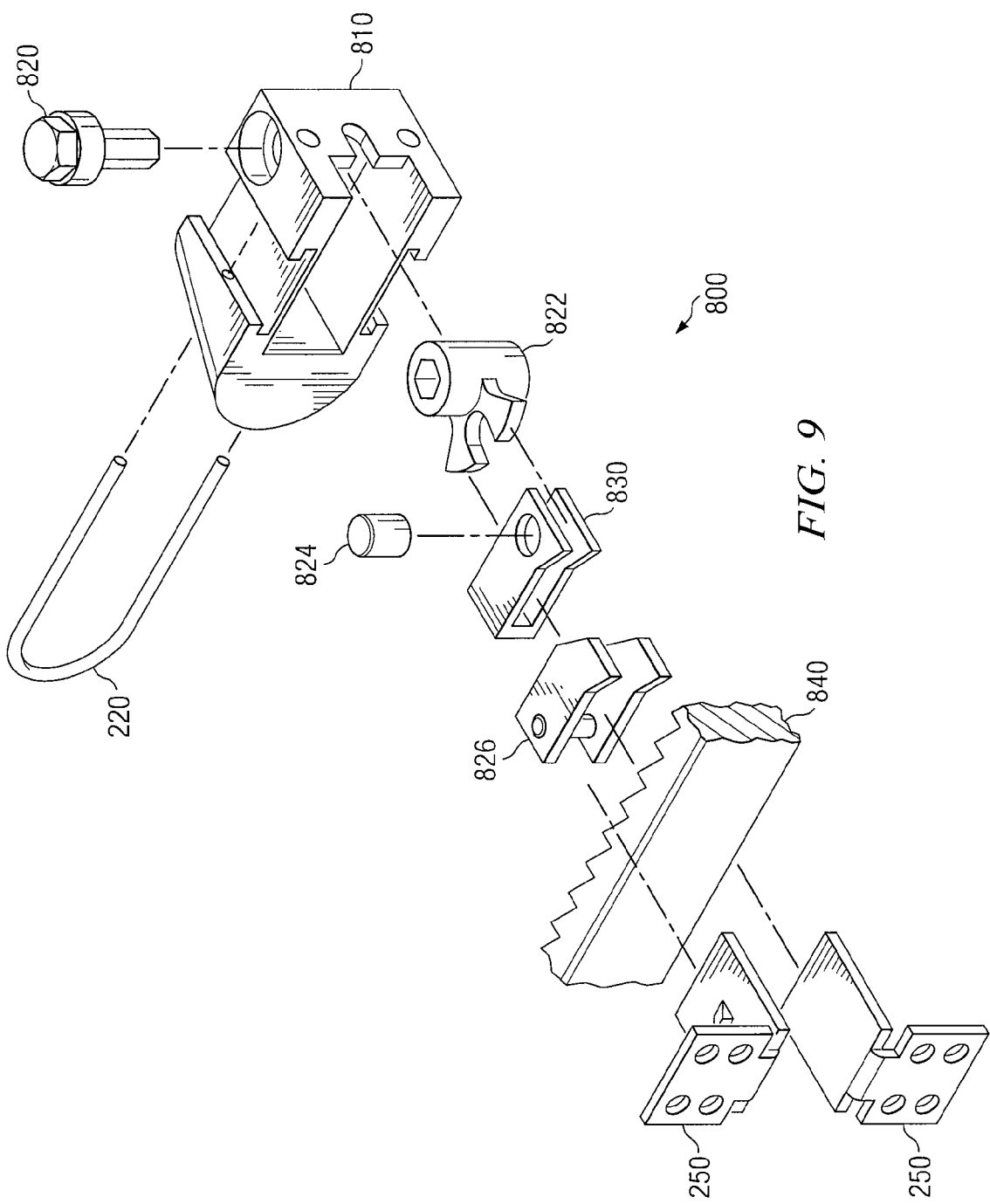
FIG. 9 illustrates an exploded view of an example mandibular bone reconstruction system.

FIG. 9 illustrates an exploded view of example mandibular bone reconstruction system 800. In various embodiments, flexible connector 220, carriage block 210, and flanges 250 are configured in the same manner as described above with respect to FIG. 2. In some embodiments, cam head 820 is configured to engage cam 822 within carriage block 812. Further, cam 822 is configured to engage actuating pawls 830 and safety pawls 826 by means of pin 824, in several embodiments. By operating cam head 820, in some embodiments, cam 822 is rotated such that actuating pawls 830 are lifted and advanced along track 840. Safety pawls 826 are, in various embodiments, situated around actuating pawls 830 and slide along track 122 as transport device 810 is advanced. Springs, in particular embodiments, may be used to keep safety pawls 826 from being lifted when actuating pawls 830 are lifted. Although these components may be made of any appropriate biocompatible materials, in some embodiments, safety pawls 826 may be made of stainless steel. Similarly, cam head 820, cam 822, pin 824, and actuating pawls 830 may, in various embodiments, be made of titanium or a titanium alloy, such as medical grade titanium alloy 6ALV4.

Track 840 may, in various embodiments, have notches with 90° faces on one side and 45° faces on the other side. In certain embodiments, track 840 may include faces with a pitch in the range of 85° to 95° on one side and may include faces with a pitch in the range of 400 to 50° on the other side. Although this component may be made of any appropriate biocompatible material, in particular embodiments, track 840 may consist of titanium or a titanium alloy, such as medical grade titanium alloy 6ALV4.

As an example only, the various embodiments described above may be used according to the following procedure. First, the maxillo-mandibular occlusion is maintained by intermaxillary wire fixation to maintain jaw relations. The appropriate length of the bone reconstruction plate (transport segment) should be estimated before surgery and a number of bone reconstruction plates with different lengths should be available during surgery to choose from. The track can be fixed to the first and second mandibular bone segments either before or after removal of the tumor segment by three bicortical screws on each side as in traditional reconstruction plate, leaving out approximately 2 cm of bone at the edge of one of the two mandibular bone segments, classically the posterior segment, so that it can be separated and fixed to the transport device. After tumor resection, the transport device is fixed to the potential bone transport plate through the flanges either before or after its separation. If immediate reconstruction is planned, a bicortical osteotomy to separate the bone transport plate is carried out during the same surgery. However, the surgeon may decide to delay the osteotomy.

During the delay period, the bone reconstruction plate will function as a traditional reconstruction plate: stabilizing the bone segment, maintaining the maxillo-mandibular occlusion, preventing soft tissue collapse, and preserving the facial symmetry. Due to its intra-oral design, the patient may tolerate it as comfortably as a traditional reconstruction plate. Reconstruction plates could be retained for years with minimal inconvenience to the patient.

Osteotomy is a procedure that takes around 15 to 30 minutes to complete. If delayed, it can be done under sedation and local anesthesia on an outpatient basis, as with the subsequent daily activation of the device. The buccal cortical plate is cut using an ultra thin micro saw and the osteotomy is then completed through the lingual cortex by a sharp osteotome. Care should be taken not to exert too much force on the transport device during bone separation. It may be helpful to separate part of the flanges from the potential bone transport plate in order to have some degree of mobility in the bone transport plate during separation. After complete separation of the bone transport plate, at least 4 secured mini-screws in total are preferred for the stability of the bone transport plate. In certain embodiments, more or less mini-screws may be used to secure the bone transport plate. The lingual mucosa should not be dissected at any time during the procedure to maintain the blood supply of the separated bone segment. The wound is then closed so that the activation cable protrudes through the mucosa into the oral cavity when the wound is closed. After 5 to 7 days of latency, activation of the device is started. The distraction rate is 0.5 mm/12 hours which may be varied by as much as 0.2 mm.

Distraction is continued until the transport segment reaches the docking site. As the bone transport plate is transported, new bone is formed behind it to gradually fill the gap. When the bone transport plate reaches the docking site (at the edge of the other bone segment), the device should be retained in place for a few weeks, depending on the amount of distraction, until the newly formed bone consolidates and is able to sustain chewing forces or carry implants. Bone grafting may still be needed to promote bone union at the docking site. In this case, freshening of bone edges and the addition of small pieces of cancellous bone may be sufficient.

Although several embodiments have been illustrated and described in detail, it will be recognized that modifications and substitutions are possible without departing from the spirit and scope of the appended claims.

What is claimed is:

1. A mandibular bone transport device comprising:
   a carriage block;
   a set of flanges separate from the carriage block, the set of flanges operable to couple to a transport bone plate;
   a flexible connector configured to flexibly couple the set of flanges to the carriage block, such that the flanges can be displaced relative to the carriage block when a force is applied;
   a screw housed within the carriage block, operable to engage a track and operable to advance the carriage block along the track; and
   a coupling configured to engage the screw and operable to rotate the screw when rotational force is applied to the coupling.

2. The device of claim 1 further comprising a threaded track.

3. The device of claim 2 wherein the threaded track is curved.

4. The device of claim 2 wherein the threaded track comprises square threads with a pitch substantially in the range from 5.5° to 10.5°.

5. The device of claim 1 wherein the screw comprises a hexagonal head and the coupling is configured to engage the hexagonal head of the screw.

6. The device of claim 1 wherein the coupling is configured to flexibly engage the screw.

7. The device of claim 1 wherein the flexible connector comprises a metallic spring.

8. The device of claim 1 wherein the carriage block comprises Grade 304 stainless steel.

9. The device of claim 1 wherein the carriage block comprises a sloped frontal portion configured to present an acute leading edge when the carriage block travels along the track.

10. A method for mandibular distraction osteogenesis, comprising:
    securing flanges to a portion of a mandible;
    securing a first end of a curved bone reconstruction plate to a first mandibular bone segment, the curved bone reconstruction plate comprising a threaded track;
    securing a second end of the curved bone reconstruction plate to a second mandibular bone segment;
    using a flexible connector, flexibly coupling the flanges to a carriage block, the flanges being separate from the carriage block, the carriage block housing a screw operable to engage the threaded track and advance the carriage block along the threaded track; and
    rotating the screw to advance the carriage block along a curved region of the track such that the carriage block is displaced relative to the flanges as the carriage block advances along the curved region of the track.

11. The method of claim 10 further comprising a coupling, wherein the screw comprises a hexagonal head and the coupling is configured to engage the hexagonal head of the screw.

12. The method of claim 10 wherein the threaded track comprises square threads with a pitch substantially in the range from 5.5° to 10.5°.

13. The method of claim 10 further comprising a coupling configured to flexibly engage the screw.

14. The method of claim 10 wherein the carriage block advances along the track at the rate of between 0.4 mm and 0.6 mm every 12 hours.

15. The method of claim 10 wherein the flexible connector comprises a metallic spring.

16. The method of claim 10 wherein the carriage block comprises Grade 304 stainless steel.

17. The method of claim 10 wherein the carriage block comprises a sloped frontal portion configured to present an acute leading edge when the carriage block travels along the threaded track.

18. A mandibular distraction osteogenesis system, comprising
    a curved, threaded track comprising:
       a first portion configured to couple to a first mandibular bone segment; and
       a second portion configured to couple to a second mandibular bone segment;
    a carriage block;
    a set of flanges separate from the carriage block, the set of flanges operable to couple to a transport bone plate;
    a flexible connector configured to flexibly couple the set of flanges to the carriage block, such that the flanges can be displaced relative to the carriage block when a force is applied;
    a screw housed within the carriage block, operable to engage a track and operable to advance the carriage block along the track; and
    a coupling coupled to the screw operable to rotate the screw when rotational force is applied to the coupling.

19. The system of claim 18, wherein the threaded track comprises square threads with a pitch substantially in the range from 5.5° to 10.5°.

20. The system of claim 18 wherein the coupling is flexible.

21. The system of claim 18 wherein the flexible connector comprises a metallic spring.

* * * * *